(12) United States Patent
Dai et al.

(10) Patent No.: US 12,426,876 B2
(45) Date of Patent: Sep. 30, 2025

(54) SUTURE LOCKING DEVICE AND SUTURE LOCKING DEVICE IMPLANTING APPARATUS

(71) Applicant: CREATIVE MEDTECH (SUZHOU) CO., LTD, Suzhou (CN)

(72) Inventors: Gaoxu Dai, Beijing (CN); Wuen Han, Beijing (CN); Fan Yang, Beijing (CN)

(73) Assignee: CREATIVE MEDTECH (SUZHOU) CO., LTD, Suzhou (CN)

(*) Notice: Subject to any disclaimer, the term of this patent is extended or adjusted under 35 U.S.C. 154(b) by 432 days.

(21) Appl. No.: 18/056,413

(22) Filed: Nov. 17, 2022

(65) Prior Publication Data

US 2023/0081274 A1 Mar. 16, 2023

Related U.S. Application Data

(63) Continuation of application No. PCT/CN2020/122560, filed on Oct. 21, 2020.

(30) Foreign Application Priority Data

May 29, 2020 (CN) .......................... 202010482438.3

(51) Int. Cl.
*A61B 17/04* (2006.01)
(52) U.S. Cl.
CPC ............................... *A61B 17/0487* (2013.01)
(58) Field of Classification Search
CPC ............ A61B 17/0487; A61B 90/50; A61B 2017/00407; A61B 17/0467;
(Continued)

(56) References Cited

U.S. PATENT DOCUMENTS 2,651,768 A * 9/1953 Oortgijsen ........... H01R 4/2458
24/130
5,152,298 A * 10/1992 Kreyenhagen ..... A61B 17/0401
607/116
(Continued)

FOREIGN PATENT DOCUMENTS

CN 107106157 A 8/2017
CN 109498216 A 3/2019
(Continued)

OTHER PUBLICATIONS

International Search Report issued in International Application No. PCT/CN2020/122560 dated Mar. 9, 2021 (6 pages).
(Continued)

*Primary Examiner* — Kathleen S Holwerda
*Assistant Examiner* — Serenity A Miller

(57) ABSTRACT

Disclosed are a suture locking device and a suture locking device implanting apparatus. The suture locking device comprises a suture pressing housing, a squeezing part and a driving component, wherein a suture pressing cavity is provided inside the suture pressing housing, the squeezing part is arranged in the suture pressing cavity, a first suture routing hole and a second suture routing hole are provided in the housing wall of the suture pressing housing, the driving component is configured to squeeze the squeezing part, and therefore, a locking suture sequentially penetrating the second suture routing hole and the first suture routing hole is squeezed.

19 Claims, 7 Drawing Sheets

(58) Field of Classification Search
CPC ........ A61B 2017/0488; A61B 17/0401; A61B 17/0469; A61B 17/0482; A61B 17/0491; A61B 2017/0409; A61B 2017/0474; A61F 2/2427; H01R 4/2466; H01R 4/2445
USPC ................ 606/139, 144, 148, 154, 157, 232
See application file for complete search history.

(56) References Cited

U.S. PATENT DOCUMENTS

| | | | | |
|---|---|---|---|---|
| 5,520,702 | A * | 5/1996 | Sauer | A61B 17/0469 606/139 |
| 9,131,939 | B1 * | 9/2015 | Call | A61B 17/0487 |
| 2011/0082538 | A1 | 4/2011 | Dahlgren et al. | |
| 2013/0158600 | A1 * | 6/2013 | Conklin | A61B 17/0401 606/232 |
| 2013/0331896 | A1 | 12/2013 | Holt | |
| 2014/0081326 | A1 * | 3/2014 | Takahashi | A61B 17/0487 606/232 |
| 2015/0272734 | A1 * | 10/2015 | Sheps | A61B 17/068 623/2.11 |
| 2016/0354080 | A1 * | 12/2016 | Sauer | A61B 17/0467 |
| 2018/0185153 | A1 | 7/2018 | Bishop et al. | |
| 2019/0029671 | A1 | 1/2019 | Zhang et al. | |
| 2019/0125325 | A1 | 5/2019 | Sheps et al. | |

FOREIGN PATENT DOCUMENTS

| | | | | |
|---|---|---|---|---|
| CN | 210612172 | U | 5/2020 | |
| CN | 111467085 | A | 7/2020 | |
| DE | 102018103977 | A1 | 8/2019 | |
| EP | 2628451 | A2 * | 8/2013 | ......... A61B 17/0401 |
| WO | 2006002492 | A1 | 1/2006 | |
| WO | 2013129114 | A1 | 9/2013 | |

OTHER PUBLICATIONS

European Office Action in corresponding European Application No. 20938475.9 dated Aug. 18, 2023 (2 pages).

* cited by examiner

SUTURE LOCKING DEVICE AND SUTURE LOCKING DEVICE IMPLANTING APPARATUS

CROSS-REFERENCE TO RELATED APPLICATIONS

The present disclosure is a continuation application of International Application No. PCT/CN2020/122560, which claims priority to Chinese Patent Application No. 202010482438.3, entitled "Suture Locking Device and Suture Locking Device Implanting Apparatus," and filed with the Chinese Patent Office on May 29, 2020, the contents of which are incorporated herein by reference in their entireties.

TECHNICAL FIELD

The present disclosure relates to the technical field of medical devices, and in particular, to a suture locking device and a suture-locking-device implanting apparatus.

BACKGROUND ART

In the medical field, it is often necessary to implant an implant into a human valve or other organ tissues or skin tissues to assist the valve closure or the suturing operations. In some cases, it may be desirable to tighten the locking sutures on at least two implants to decrease the distance between the at least two implants. In some cases, it is necessary to tie the ends of the sutured surgical suture, for preventing the sutures from being disengaged. For these two cases, at present, it is mainly adopted that doctors use instruments to manually tie knots, wherein the problems are that: the knotting is difficult, doctors of high technical level are required, the knotting efficiency is low, and it is easy to prolong the operation time, thereby increasing risks in operation.

SUMMARY

The embodiment of the present disclosure provides a suture locking device, comprising a suture pressing housing, a squeezing part (pressing part) and a driving component, wherein
  a suture pressing cavity is provided inside the suture pressing housing;
  the squeezing part is arranged inside the suture pressing cavity; and a first suture routing hole and a second suture routing hole are formed on a housing wall of the suture pressing housing;
  the driving component is mounted at the suture pressing housing, and the driving component is configured to be able to move towards a cavity wall of the suture pressing cavity relative to the suture pressing housing under a condition of locking a suture, so as to squeeze/press the squeezing part, such that a locking suture that passes through the second suture routing hole and the first suture routing hole in sequence is pressed between the squeezing part and the cavity wall of the suture pressing cavity.

The embodiment of the present disclosure also provides a suture-locking-device implanting apparatus, comprising an implanting assembly and the suture locking device according to any one of foregoing embodiments, wherein the implanting assembly is configured to implant the suture locking device into a human body.

BRIEF DESCRIPTION OF DRAWINGS

In order to illustrate the embodiments of the present disclosure or the technical solutions in the prior art more clearly, the drawings that need to be used in the description of the embodiments or the prior art will be briefly introduced below. Obviously, the drawings in the following description show some embodiments of the present disclosure. For those skilled in the art, other drawings can also be obtained based on these drawings without creative efforts.

Figure 1:
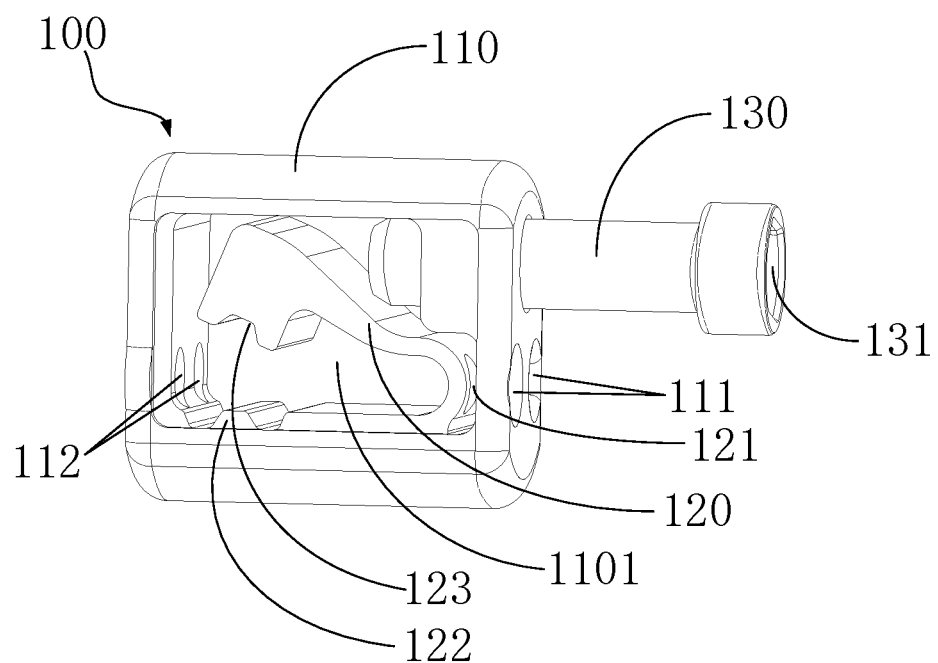
FIG. 1 is a perspective view of the overall structure of an optional implementation of the suture locking device provided by the embodiment of the present disclosure.

Reference Numbers: 100—suture locking device; 110—suture pressing housing; 1101—suture pressing cavity; 111—first suture routing hole; 112—second suture routing hole; 120—squeezing part; 121—third suture routing hole; 122—snapping protrusion; 123—snapping groove; 130—driving component; 131—first limit part; 141—suture cutting shell; 142—suture cutting blade; 143—suture passing hole; 144—operation hole; 200—mounting seat; 310—suture passing handle; 311—first suture passing handle; 312— second suture passing handle; 320—implanting handle; 3200—anti-reversal structure; 3201—ratchet; 3202—pawl member; 321—main body tube; 3210—main body tube limiting hole; 3211—middle connection rod; 322—rotating shell; 323—compensation mechanism; 3231—compensation knob; 3232—compensation sleeve; 32321—inner pattern structure; 32322—polygon limiting hole; 3233—connection screw rod; 3234—polygon snapping head; 330—implanting cable; 331—second limit part; 340—adjustment frame; 400—locking-suture adjustment mechanism; 410—first locking suture fixing structure; 420—second locking suture fixing structure; 421—connection seat; 4210—limiting groove; 422—adjustment knob; 423—adjustment screw rod; 424—sliding block; 4240—locking part; 500—suture passing tube; 600—handle housing; 610—avoidance hole; 700—branch tube; 710—first branch cavity; 720—second branch cavity; 800—bending-adjusting handle; 810—bending-adjusting knob; 820—bending-adjusting screw rod; 830—bending-adjusting sliding block; 840—rotating structure; 841—upper half shell; 842—lower half shell; 843—fastener; 900—bending-adjusting sheath tube; 1000—sealing seat; 2000—supporting structural member; 3000—sealing gasket.

DETAILED DESCRIPTION OF EMBODIMENTS

In order to make the purposes, technical solutions and advantages of the embodiments of the present disclosure clearer, the technical solutions in the embodiments of the present disclosure will be clearly and completely described below with reference to the drawings in the embodiments of the present disclosure. Obviously, some, but not all, of the embodiments of the present disclosure are described. Generally, the components of the embodiments, shown and illustrated in the drawings herein, may be arranged and designed in a variety of different configurations.

Therefore, the following detailed description on the embodiments of the disclosure provided in the drawings is not intended to limit the scope of the disclosure as claimed, but merely representative of selected embodiments of the disclosure. Based on the embodiments in the present disclosure, all other embodiments, which are obtained by those skilled in the art without creative efforts, shall fall within the protection scope of the present disclosure.

It should be noted that similar numerals and letters refer to similar items in the following figures, and thus once an item is defined in one figure, it is not required to further define and explain it in subsequent figures.

In the description on the present disclosure, it should be noted that the orientation or position relationships, indicated by the terms, such as, "upper", "lower", "vertical", "horizontal", "inner", "outer", etc., are based on the orientation or position relationship shown in the drawings, or the orientation or position relationship in which the product of the invention is usually placed in use. It is only for the convenience of describing the present disclosure and simplifying the description, rather than indicating or implying that the device or element referred to must be in the specific orientation, or constructed and operated in a particular orientation, and therefore should not be construed as a limitation on the present disclosure. Furthermore, the terms, "first", "second", "third", etc., are only used to describe the distinguishing and should not be construed as indicating or implying the importance of relativity.

Furthermore, the terms, "horizontal", "vertical" and the like, do not indicate that a component is required to be absolutely horizontal or overhang, but may be slightly inclined. For example, "horizontal" only means that its direction is more horizontal than the "vertical", and it does not mean that the structure must be completely horizontal, but can be slightly inclined.

In the description of the present disclosure, it should also be noted that, unless expressly specified and limited otherwise, the terms "arrangement", "installation" and "connection" should be construed in a broad sense. For example, it may be a fixed connection or a detachable connection, or integral connection; may be the mechanical connection or the electrical connection; may be the direct connection, or the indirect connection through an intermediate medium, or the internal communication between two components. For those skilled in the art, the specific meanings of the above terms in the present disclosure can be understood in specific situations.

The suture locking device and the suture-locking-device implanting apparatus provided by the present disclosure can alleviate the technical problems in the prior art that the knotting is difficult, the knotting efficiency is low, and the operation time is easily prolonged, thereby increasing the risk in operation.

Some embodiments of the present disclosure will be described in detail below with reference to the drawings. The embodiments described below and features in the embodiments may be combined with each other without conflict.

This embodiment provides a suture locking device 100. Referring to FIG. 1, the suture locking device 100 comprises a suture pressing housing 110, a squeezing part 120 and a driving component 130.

Specifically, a suture pressing cavity 1101 is provided inside the suture pressing housing 110, the squeezing part 120 is arranged inside the suture pressing cavity 1101, and a first suture routing hole 111 and the second suture routing hole 112 are formed on the housing wall of the suture pressing housing 110. The driving component 130 is installed on the suture pressing housing 110, and the driving component 130 is configured to be able to move towards the cavity wall of the suture pressing cavity 1101 relatively to the suture pressing housing 110 under the condition of locking the suture, so as to squeeze the squeezing part 120, so that the locking suture passing through the second suture routing hole 112 and the first suture routing hole 111 in sequence is squeezed to be located between the squeezing part 120 and the cavity wall of the suture pressing cavity 1101.

In use, the suture locking device 100 is sleeved on the surgical suture, outside the human body, that is, the end of the surgical suture away from the human body is made to pass through the second suture routing hole 112 and the first suture routing hole 111 on the suture locking device 100 in sequence, then the surgical delivery instrument and the bending-adjusting sheath tube are used to implant the suture pressing housing 110 into the human body, and then the driving component 130 is driven, so that the driving component 130 squeezes the squeezing part 120, and then the locking suture which passes through the second suture routing hole 112 and the first suture routing hole 111 in sequence is squeezed by the squeezing part 120, and the locking suture is squeezed to be located between the squeezing part 120 and the cavity wall of the suture pressing cavity, to complete the work of locking the suture.

Compared with the existing solution in which the medical staff manually knots the locking sutures of at least two implants or the sutured surgical suture, the suture locking device 100 provided by the embodiment of the present disclosure is of a simple and convenient structure, which is beneficial for reducing dependence on technology of the medical staff, improving the efficiency of locking the suture, shortening the operation time, and reducing the risk in operation.

In an optional implementation of the embodiment of the present disclosure, the above-mentioned squeezing part 120 may be of a flat plate structure, and the squeezing part 120 is fixedly connected to the driving component 130. In this way, when the driving component 130 is moving, the squeezing part 120 can be driven to move, thereby driving the squeezing part 120 to squeeze the locking suture. In addition, the squeezing part can also be movably installed inside the suture pressing housing 110.

In this embodiment, one end of the squeezing part 120 is connected to the inner wall of the suture pressing cavity 1101, and the squeezing part 120 is an elastic sheet. It should be noted that, in this embodiment, after the driving component 130 acts on the squeezing part 120, the distance between the other end of the squeezing part 120 and the inner wall of the suture pressing cavity 1101 is reduced, and the squeezing part 120 can squeeze the locking suture passing through the second suture routing hole 112 and the first suture routing hole 111. After the driving component 130 is disengaged from the squeezing part 120, the squeezing part 120 can return to the initial state under the action of its own restoring force, which facilitates the installation and movement of the locking suture.

The above-mentioned squeezing part 120 is an elastic sheet. One end of the elastic sheet, after being bent, is connected to the cavity wall of the suture pressing cavity, and the elastic sheet is configured to have a rotation gap between it and the cavity wall of the suture pressing cavity which is connected with the elastic sheet, in the initial state. A third suture routing hole 121 is formed on the elastic sheet, and the driving component 130 is configured to be able to move, relatively to the suture pressing housing 110, towards the cavity wall of the suture pressing cavity which is connected with the elastic sheet, under the condition of locking the suture, so as to squeeze the elastic sheet, so that the locking suture passing through the second suture routing hole 112, the third suture routing hole 121 and the first suture routing hole 111 in sequence is squeezed to be located between the elastic sheet and the cavity wall of the suture pressing cavity.

It should be noted that the elastic sheet may be made of metal, but not limited thereto.

During the process that the locking suture passing through the second suture routing hole 112, the third suture routing hole 121 and the first suture routing hole 111 in sequence is squeezed by the elastic sheet to be located between the elastic sheet and the cavity wall of the suture pressing cavity, the position at which the elastic sheet and the cavity wall of the suture pressing cavity are attached to each other is fixed, which can improve the accuracy of the locking suture being squeezed at a fixed position and avoid the failure of locking the suture.

In this embodiment, since one end of the squeezing part 120 is connected to the cavity wall of the suture pressing cavity, in the process of the driving component 130 driving the squeezing part 120, the relative positions of one end of the squeezing part 120 which is connected to the inner wall of the suture pressing cavity 1101 is at a relative position with respect to the inner wall of the suture pressing cavity 1101, with the relative position remaining unchanged, which can ensure that the squeezing part 120 squeezes the locking suture more accurately and reduces the probability of failure of locking the suture.

Referring to FIG. 1, in this embodiment, the squeezing part 120 is provided with a third suture routing hole 121. And the first suture routing hole 111, the third suture routing hole 121 and the second suture routing hole 112 are communicated in sequence. It can be understood that the locking suture can pass through the second suture routing hole 112, the third suture routing hole 121 and the first suture routing hole 111 in sequence. A part of the locking suture is correspondingly arranged between the squeezing part 120 and the inner wall of the suture pressing cavity 1101. After the driving component 130 acts on the squeezing part 120, the squeezing part 120 can squeeze the part of the locking suture, thereby locking the locking suture.

A snapping protrusion 122 is provided on one of the cavity wall of the suture pressing cavity connected with the elastic sheet, and the side of the elastic sheet facing the cavity wall connected with the elastic sheet. An snapping groove 123 capable of being engaged with the snapping protrusion 122 is provided on the other one of the cavity wall of the suture pressing cavity connected with the elastic sheet, and the side of the elastic sheet facing the cavity wall connected with the elastic sheet.

That is to say, in this embodiment, a snapping protrusion 122 is provided on the side wall of the suture pressing cavity 1101, and a snapping groove 123 is concavely provided on the side of the squeezing part 120 close to the snapping protrusion 122. It can be understood that, after the driving component 130 acts on the squeezing part 120, the squeezing part 120 squeezes the locking suture, and the snapping protrusion 122 can be embedded in the snapping groove 123 to lock the locking suture.

It should be noted that, in this embodiment, by providing the above-mentioned snapping protrusion 122 and snapping groove 123, the driving component 130, during the process of squeezing the squeezing part 120, can make the locking suture, which passes through the second suture routing hole 112, the third suture routing hole 121 and the first suture routing hole 111 in sequence, squeezed between the snapping protrusion 122 and the snapping groove 123, increasing the firmness of the locking suture being locked.

In addition, the driving component 130 may be provided in various specific arrangement. An example is as follows, but the present disclosure is not limited thereto. The driving component 130 comprises a driving rod, an elastic snap is provided on the driving rod, and a snapping hole is provided on the suture pressing housing 110. A spring is arranged between the driving rod and the cavity wall of the suture pressing cavity, and the driving rod can compress the spring under the action of the driving force to squeeze the squeezing part 120. During this process, the elastic fastener slides closely to the cavity wall of the suture pressing cavity. When the locking suture passing through the second suture routing hole 112 and the first suture routing hole 111 in sequence is squeezed, the elastic fastener on the driving rod passes through the snapping hole to fix the driving rod.

Continuously referring to FIG. 1, an external thread is provided on the outer peripheral surface of the driving component 130, the housing wall of the suture pressing housing 110 is provided with a threaded hole running through the housing wall, and the driving component 130 is screwed into the threaded hole, the driving component 130 is configured to be able to rotate relatively to the suture pressing housing 110 to move toward the cavity wall of the suture pressing cavity, under the condition of locking the suture, so as to squeeze the squeezing part 120.

That is to say, in this embodiment, an external thread is provided on the outer peripheral surface of the driving component 130, the suture pressing housing 110 is provided with a threaded hole communicating with the suture pressing cavity 1101, and the external thread threadedly cooperates with the threaded hole.

In this way, the driving component 130 is rotated, the driving component 130 can reciprocate along the axial direction of the threaded hole, and the driving component 130 can abut against or be disengaged from the squeezing part 120.

Figure 2:
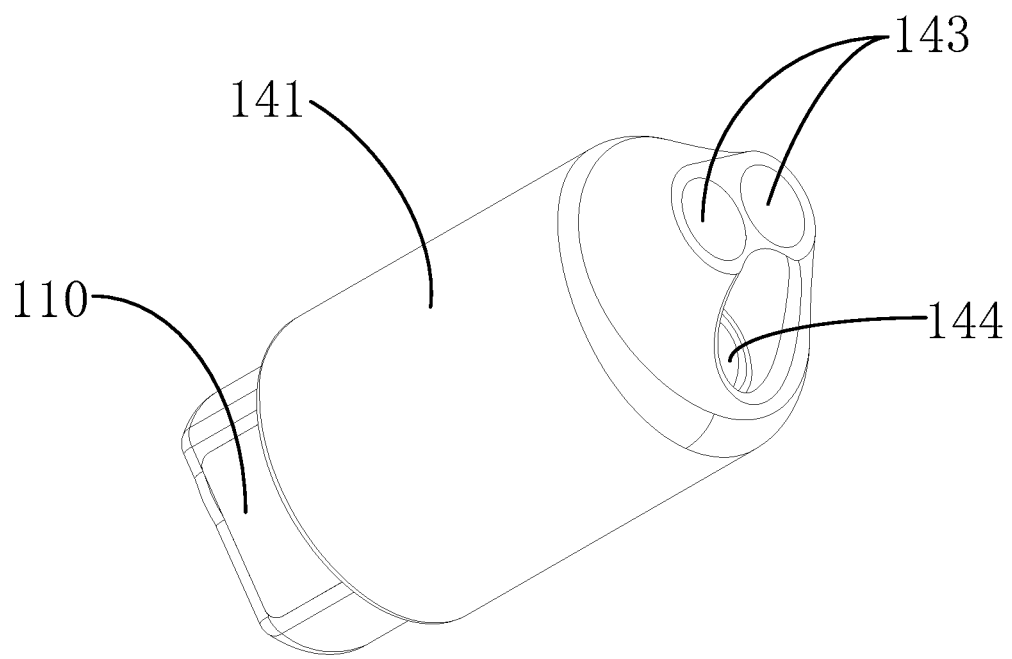
FIG. 2 is a schematic diagram of the overall structure of another optional implementation of the suture locking device provided by the embodiment of the present disclosure.
Figure 3:
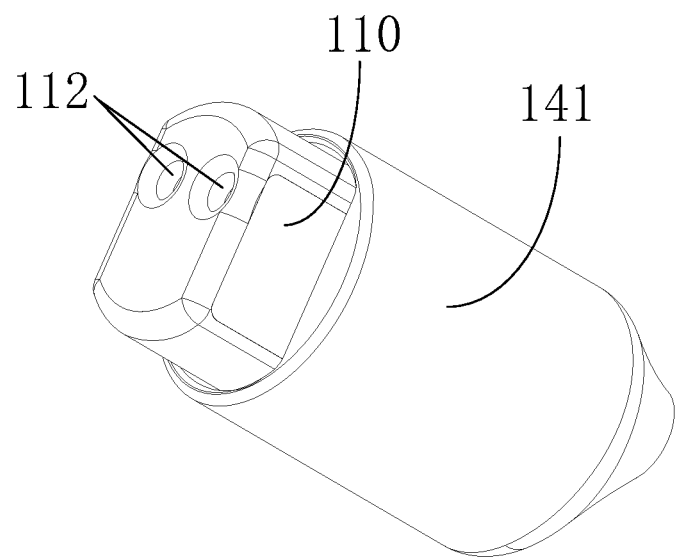
FIG. 3 is a schematic diagram of the overall structure of the suture locking device provided in FIG. 2 from another perspective.
Figure 4:
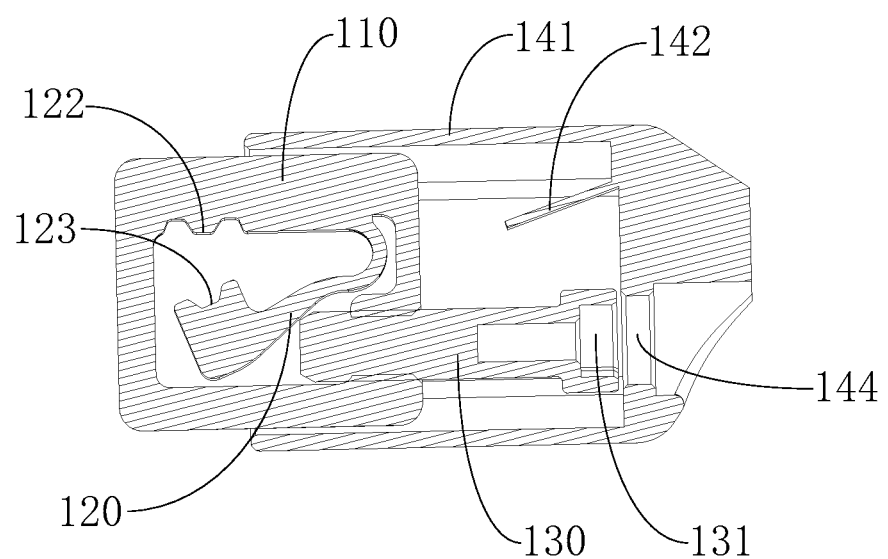
FIG. 4 is a sectional view of the suture locking device shown in FIG. 2.

Referring to FIGS. 2, 3 and 4, in conjunction with FIG. 1, the suture locking device 100 further comprises a suture cutting structure, the suture cutting structure comprises a suture cutting shell 141 and a suture cutting blade 142, and one end of the suture cutting shell 141 is sleeved over the suture pressing housing 110, the suture cutting shell 141 covers the first suture routing hole 111, the suture cutting blade 142 is connected with the suture cutting shell 141, and the suture cutting blade 142 is configured to cut the locking suture.

In actual use, after the locking suture is locked by the squeezing part 120, the suture cutting blade 142 can cut off the locking suture, which shortens the time for cutting the suture during the operation and improves the surgical operation efficiency.

Specifically, in this embodiment, the suture cutting shell 141 is provided with a suture passing hole 143, the suture passing hole 143 communicates with the first suture routing hole 111, the suture cutting blade 142 is located inside the suture cutting shell 141, and the suture cutting blade 142 is configured to cut the locking suture that passes through the suture passing hole 143 and the first suture routing hole 111.

It can be understood that the locking suture can extend into the suture cutting shell 141 after passing through the first suture routing hole 111 and the suture passing hole 143, and the suture cutting blade 142 is located inside the suture cutting shell 141, which is convenient for the suture cutting blade 142 to cut the locking suture.

Specifically, in this embodiment, in the case that the driving component 130 rotates relatively to the suture pressing housing 110, the suture cutting shell 141 and the suture pressing housing 110 can move toward each other to squeeze the suture cutting blade 142, thereby making the suture cutting blade 142 cut the locking suture passing through the suture passing hole 143 and the first suture routing hole 111. In use, after the driving component 130 squeezes the squeezing part 120 toward the cavity wall of the suture pressing cavity, the suture cutting blade 142 cuts the locking suture passing through the suture passing hole 143 and the first suture routing hole 111, and then cuts off the locking suture, which is beneficial to save the time for cutting the suture during the operation and further speed up the surgical operation efficiency.

In an optional implementation, one end of the suture cutting shell 141 is sleeved over the outside of the end of the suture pressing housing 110 where the first suture routing hole 111 is formed, and the shell wall of the other end of the suture cutting shell 141 is provided with the suture passing hole 143 and the operation hole 144 running through the housing wall. The suture cutting blade 142 is arranged inside the suture cutting shell 141, and one end of the suture cutting blade 142 is connected to the inner wall of the shell body of the suture cutting shell 141. Under the condition that the driving component 130 rotates relatively to the suture pressing housing 110, the suture cutting shell 141 and the suture pressing housing 110 can move toward each other, so as to squeeze the suture cutting blade 142, and then make the suture cutting blade 142 cut the locking suture passing through the suture passing hole 143 and the first suture routing hole 111. In use, the squeezing part 120 can be squeezed by the driving component 130 toward the cavity wall of the suture pressing cavity, and finally after the locking suture passing through the second suture routing hole 112 and the first suture routing hole 111 in sequence is squeezed to be located between the squeezing part 120 and the cavity wall of the suture pressing cavity, the suture cutting blade 142 cuts the locking suture passing through the suture passing hole 143 and the first suture routing hole 111, and then cuts the locking suture, which is beneficial to save the time for cutting the suture in the operation, to further speed up the surgical operation efficiency.

Referring to FIG. 4, in this embodiment, the suture cutting shell 141 is further provided with an operation hole 144, and the operation hole 144 communicates with the inner cavity of the suture cutting shell 141. The operation hole 144 can be externally connected to the implanting assembly, so that the implanting assembly can implant the suture locking device into the human body.

Specifically, the present embodiment also provides a suture-locking-device implanting apparatus. The suture-locking-device implanting apparatus comprises an implanting assembly and the aforementioned suture locking device. The implanting assembly is configured to implant the suture locking device into the human body. The use of suture-locking-device implanting apparatus provided in this embodiment is convenient and efficient, which is beneficial to quickly implant the suture locking device 100 into the human body, and can also reduce dependence on technology of the medical staff, improve the efficiency of locking the suture, shorten the operation time, and reduce the risk in operation.

Specifically, referring to FIGS. 5 to 16, the suture-locking-device implanting apparatus further comprises a mounting seat 200, the implanting assembly comprises a suture passing handle 310, an implanting handle 320 and an implanting cable 330, wherein the implanting handle 320 and the suture passing handle 310 are both mounted on the mounting seat 200, the suture passing handle 310 is provided with a suture routing cavity for allowing the locking suture to pass therethrough, the proximal end of the implanting cable 330 is connected to the implanting handle 320, and the implanting handle 320 is configured to be able to drive the implanting cable 330 to rotate, the distal end of the implanting cable 330 is sleeved on the driving component 130, and the implanting handle 320 is configured to drive the implanting cable 330 and the driving component 130 to rotate synchronously.

Figure 7:
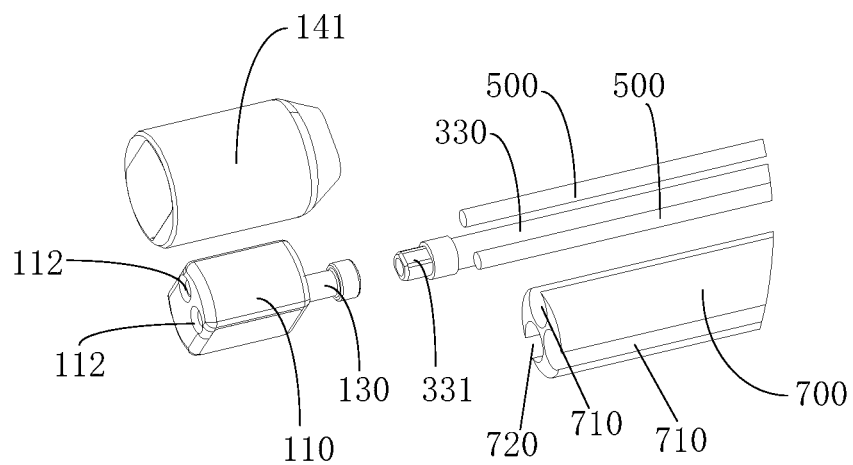
FIG. 7 is the exploded structural schematic diagram of FIG. 6.

It should be noted that, in this embodiment, the aforementioned "proximal end" and "distal end" are defined by referring to the position of the suture-locking-device implanting apparatus relative to the operator when normally working. For example, in the suture-locking-device implanting apparatus, the end relatively closer to the operator is the "proximal end", and the end relatively far away from the operator is the "distal end". That is to say, specifically, as shown in FIG. 4, a first limit part 131 is provided on the end surface of one end of the driving component 130 away from the squeezing part 120. As shown in FIG. 7, the distal end of the implanting cable 330 is provided with a second limit part 331. One of the first limit part 131 and the second limit part 331 is of a polygonal convex structure, and the other one of the first limit part 131 and the second limit part 331 is of the limiting groove structure. The distal end of the implanting cable 330 is sleeved on one end of the driving component 130 away from the squeezing part 120, in the way that the second limit part 331 is fastened to the first limit part 131 and it is ensured that the driving component 130 rotates synchronously with the implanting cable 330.

For example, the first limit part 131 is of a polygonal convex structure, the second limit part 331 is of a limiting groove structure, and the first limit part 131 and the second limit part 331 are engaged with each other, so as to ensure that the implanting cable 330 rotates synchronously with the driving component 130.

It should be noted that, in other embodiments, the first limit part 131 may also be of a limiting groove structure, the second limit part 331 may also be of a polygonal convex structure, the first limit part 131 and the second limit part 331 can also be engaged with each other, so as to ensure that the implanting cable 330 and the driving component 130 rotate synchronously.

Referring to FIGS. 11 to 14, the implanting handle 320 comprises a main body tube 321 and a rotating shell 322, the main body tube 321 is slidably mounted on the mounting seat 200, and the distal end of the rotating shell 322 is rotatably connected to the proximal end of the main body tube 321. The implanting cable 330 passes through the main body tube 321, and the proximal end of the implanting cable 330 is connected to the distal end of the rotating shell 322, and the rotating shell 322 is configured to be able to drive the implanting cable 330 to rotate.

In this embodiment, the suture cutting shell 141 and the suture pressing housing 110 can move toward each other, so that the suture pressing housing 110 has a movement tendency to withdraw from the human body in the direction toward the implanting cable 330, or that the suture pressing housing 110 is made to actually retreat by a short distance, which will reduce the effect of locking the suture.

Figure 8:
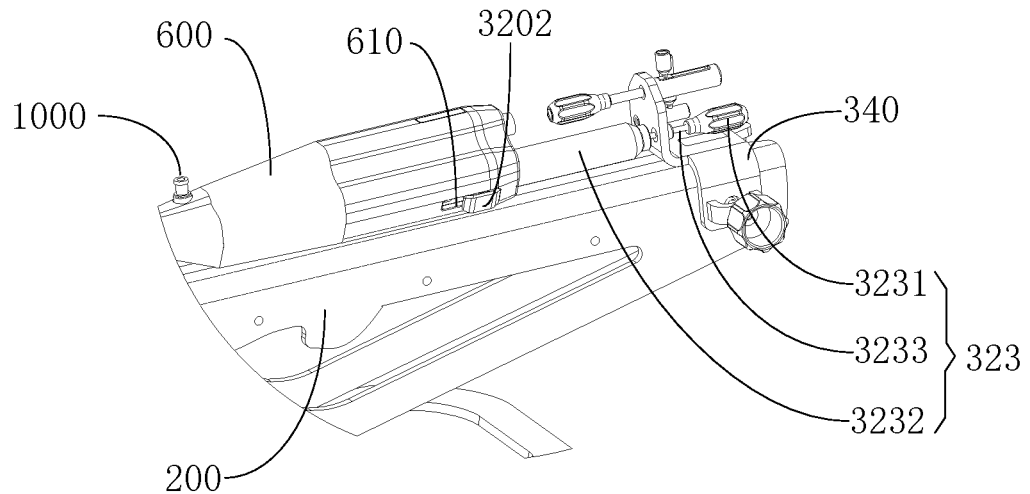
FIG. 8 is an enlarged view of the partial structure of Part B in FIG. 5.

For eliminating this effect, referring to FIGS. 3 and 8, the implanting handle 320 further comprises an adjustment frame 340 and a compensation mechanism 323, the adjustment frame 340 is connected to the mounting seat 200, the compensation mechanism 323 is in transmission connection with the adjustment frame 340, and the compensation mechanism 323 is connected to the rotating shell 322.

It should be noted that, the connection between the adjustment frame 340 and the mounting seat 200 may be the screw connection, welding, bonding, or the like.

It should be noted that, in this embodiment, the compensation mechanism 323 is configured to drive the rotating shell 322 to rotate relatively to the mounting seat 200 and meanwhile move back and forth relatively to the mounting seat 200. In this way, when the implanting cable 330 is pushed, the main body tube 321 slides relatively to the mounting seat 200, and the main body tube 321 and the rotating shell 322 act together to avoid that the main body tube 321 hinders the movement of the rotating shell 322 relative to the mounting seat 200.

Specifically, in this embodiment, the compensation mechanism 323 comprises a compensation sleeve 3232 and a compensation knob 3231, the compensation sleeve 3232 is sleeved on the outside of the rotating shell 322, the distal end of the compensation knob 3231 is provided with a connection screw rod 3233, and the adjustment frame 340 is provided with a threaded hole, the connection screw rod 3233 threadedly cooperates with the threaded hole, and the distal end of the connection screw rod 3233 is engaged with the proximal end of the compensation sleeve 3232.

It can be understood that, in this embodiment, the compensation knob 3231 is rotated, the compensation knob 3231 can drive the connection screw rod 3233 to rotate, thereby driving the rotating shell 322 to rotate relatively to the mounting seat 200 and meanwhile move back and forth relatively to the mounting seat 200, thereby achieving the effect of preventing the main body tube 321 from hindering the movement of the rotating shell 322 relative to the mounting seat 200.

The adjustment frame 340 can be fixed to the mounting seat 200 in a detachable manner by screws or other connecting parts or fixed to the mounting seat by welding. The compensation mechanism 323 comprises a compensation knob 3231 and a compensation sleeve 3232. The compensation sleeve 3232 is sleeved on the outside of the rotating shell 322 in the way of rotating synchronously with the rotating shell 322. The distal end of the compensation knob 3231 is connected with a connection screw rod 3233, the adjustment frame 340 is provided with a threaded hole, and the connection screw rod 3233, in the way of being threadedly connected to the inside of the threaded hole, passes through the adjustment frame 340, and the distal end of the connection screw rod 3233 is engaged with the proximal end of the compensation sleeve 3232, the compensation knob 3231 is configured to be able to drive the connection screw rod 3233 to rotate, thereby driving the rotating shell 322 to rotate relatively to the mounting seat 200 and meanwhile move back and forth relatively to the mounting seat 200, whereby the implanting cable 330 is pushed forward relatively to the mounting seat 200, and the main body tube 321 is slidably installed on the mounting seat 200, so that the main body tube 321 and the rotating shell 322 act together, so as to prevent the main body tube 321 from hindering the forward movement of the rotating shell 322 relative to the mounting seat 200.

It should be noted that, in an optional implementation, the compensation sleeve 3232 may be manufactured as integrally formed with the rotating shell 322, and the compensation sleeve 3232 may also be connected with the rotating shell 322 by screws. In this way, it is convenient for the compensation sleeve 3232 to rotate synchronously with the rotating shell 322.

Figure 11:
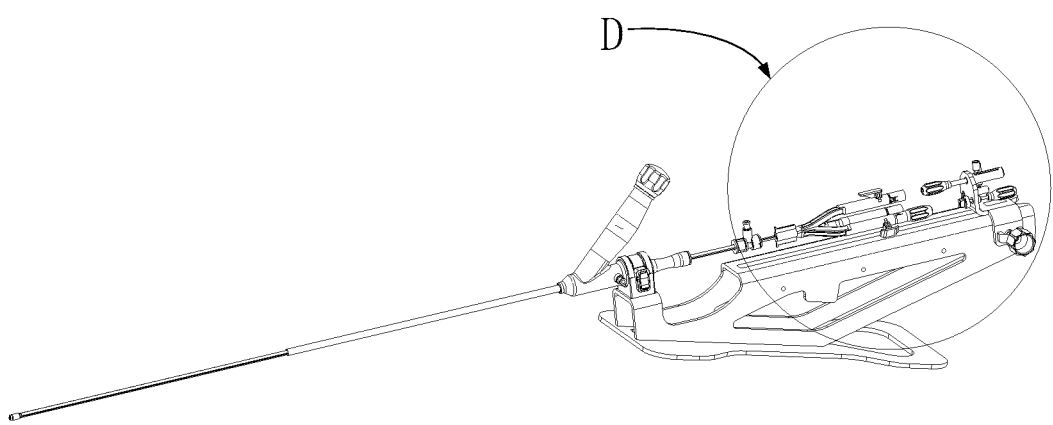
FIG. 11 is a schematic diagram of the overall structure of the suture-locking-device implanting apparatus provided in the embodiment of the present disclosure, in the condition of the suture locking device being installed and the handle housing and the compensation sleeve not being installed.
Figure 12:
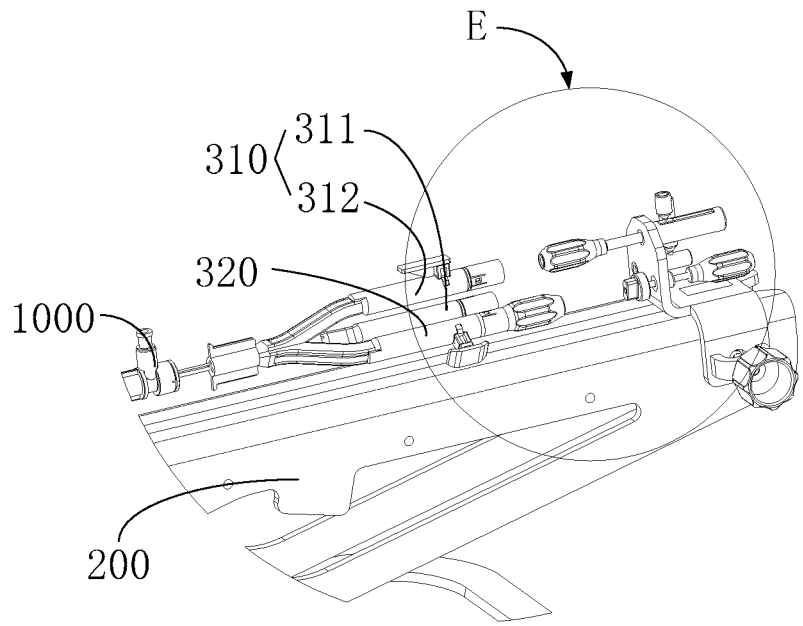
FIG. 12 is an enlarged view of the partial structure of part D in FIG. 11.
Figure 13:
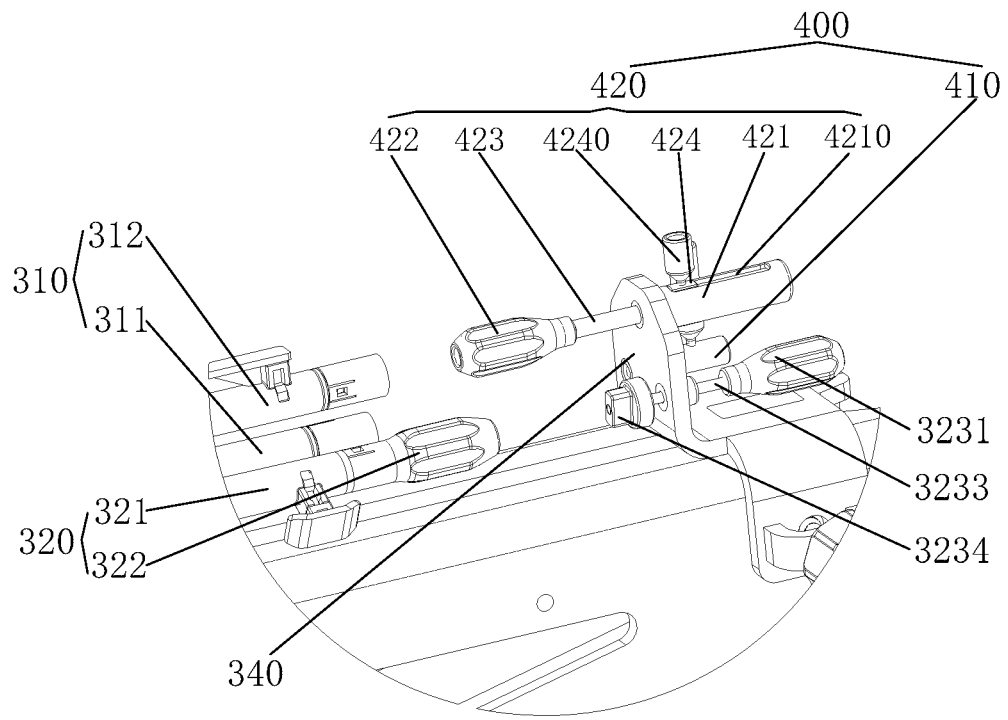
FIG. 13 is an enlarged view of the partial structure of part E in FIG. 12.
Figure 15:
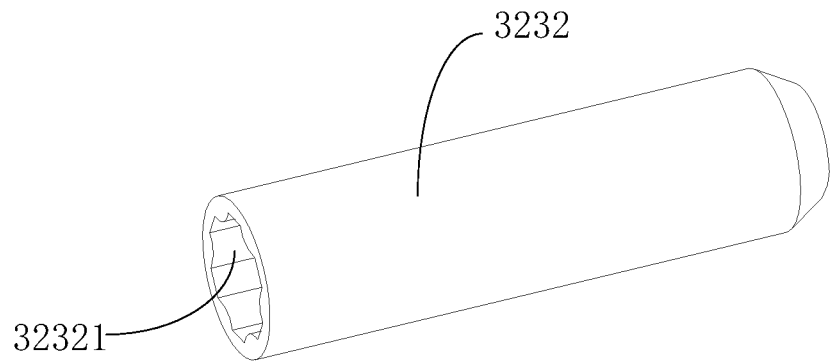
FIG. 15 is a schematic diagram of the overall structure of a compensation sleeve of a suture-locking-device implanting apparatus provided by an embodiment of the present disclosure from one perspective.

Specifically, in this embodiment, as shown in FIGS. 13 and 15, in conjunction with FIGS. 11 and 12, the outer surface of the rotating shell 322 is formed with an outer pattern structure, and the inner wall of the compensation sleeve 3232 is formed with an inner pattern structure 32321 interlocking with the aforementioned outer pattern structure. In this way, after the outer pattern structure and the inner pattern structure 32321 are interlocked with each other, it can be effectively ensured that the compensation sleeve 3232 rotates synchronously with the rotating shell 322, so as to facilitate the disassembly and assembly of the rotating shell 322.

Figure 16:
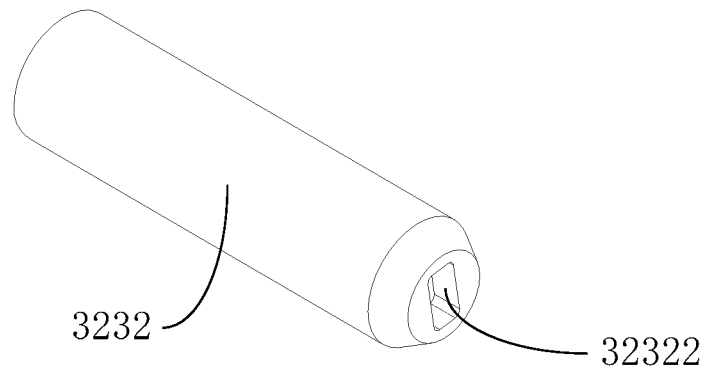
FIG. 16 is a schematic diagram of the overall structure of the compensation sleeve provided in FIG. 15 from another perspective.

As shown in FIGS. 13 and 16, the specific way in which the distal end of the connection screw rod 3233 is engaged with the proximal end of the compensation sleeve 3232 may be, but not limited to, that a snapping head 3234 of a polygonal shape is provided on the end face of the distal end of the connection screw rod 3233, and a limiting hole 32322 of a polygonal shape is provided on the end face of the proximal end of the compensation sleeve 3232. The polygonal snapping head 3234 cooperates with the polygonal limiting hole 32322 to realize the mutual engagement between the connection screw rod 3233 and the compensation sleeve 3232.

Figure 14:
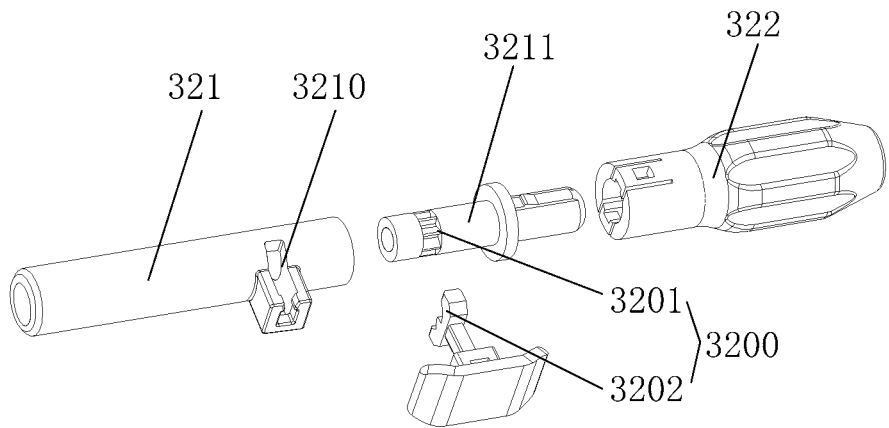
FIG. 14 is an exploded view of a partial structure of the implanting handle shown in FIG. 13.

In addition, in this embodiment, as shown in FIG. 14, an anti-reversal structure 3200 is also provided between the distal end of the rotating shell 322 and the main body tube 321, and the anti-reversal structure 3200 can effectively avoid the problem that the rotating shell 322 is reversed due to the doctor's mis-operation.

Specifically, in this embodiment, a middle connection rod 3211 is connected to the distal end of the rotating shell 322, and the middle connection rod 3211 extends into the inside of the proximal end of the main body tube 321. The anti-reversal structure 3200 comprises a ratchet 3201 and a pawl member 3202, the ratchet 3201 is arranged on the outer wall of the middle connection rod 3211, and the tube wall of the main body tube 321 is provided with a main body tube limiting hole 3210, and the pawl member 3202 passes through the main body tube limiting hole 3210, and the pawl member 3202 is engaged with the ratchet 3201. In this way, the rotating shell 322 can be effectively prevented from being reversed. It should be noted that, in this embodiment, "forward rotation" can be understood as the rotation direction of the rotating shell 322 when it works normally, and "reverse rotation (reversed)" can be understood as the opposite direction to the "forward rotation".

Referring to FIG. 1, in this embodiment, the first suture routing holes 111 and the second suture routing holes 112 are in the number of two respectively, and they are in one-to-one correspondence. In conjunction with FIGS. 11 to 13, the suture passing handle 310 comprises a first suture passing handle 311 and a second suture passing handle 312. The first suture passing handle 311 and the second suture passing handle 312 are both installed on the mounting seat 200. The first suture passing handle 311 and the second suture passing handle 312 are each provided therein with respective suture passing cavities, and the suture passing cavity in the first suture passing handle 311 and the suture passing cavity in the second suture passing handle 312 are communicated with corresponding first suture routing holes 111.

Referring to FIG. 13, in conjunction with FIGS. 11 and 12, the suture-locking-device implanting apparatus further comprises an adjustment frame 340 and a locking suture adjustment mechanism 400, the adjustment frame 340 is fixed to the mounting seat 200, and the locking suture adjustment mechanism 400 comprises the first locking suture fixing structure 410 and the second locking suture fixing structure 420, the first locking suture fixing structure 410 and the second locking suture fixing structure 420 are both connected to the adjustment frame 340, and the first locking suture fixing structure 410 is configured to be able to fix the locking suture extending out from the first suture passing handle 311, and the second locking suture fixing structure 420 is configured to be able to fix the locking suture extending out through the second suture passing handle 312.

In an optional implementation, the adjustment frame 340 can be fixed to the mounting seat 200 in a detachable manner by screws or other connection members, or fixed to the mounting seat by welding, and the adjustment frame 340 is located rear of the first suture passing handle 311 and the second suture passing handle 312. In particular, referring to FIG. 13, in this embodiment, the second locking suture fixing structure 420 comprises a connection seat 421 and a sliding block 424. The connection seat 421 is fixedly connected to the adjustment frame 340, and the connection seat 421 is provided with the limiting groove 4210, the sliding block 424 is slidably arranged in the limiting groove 4210, the sliding block 424 is provided thereon with a locking part 4240, the locking part 4240 extends out through the limiting groove 4210, and the locking part 4240 is configured to be able to lock the locking suture extending out from the second suture passing handle 312.

The second locking suture fixing structure 420 further comprises an adjustment screw rod 423 and an adjustment knob 422, the adjustment screw rod 423 passes through the adjustment frame 340 and extends into the limiting groove 4210, and the adjustment knob 422 is connected to one end of the adjustment screw rod 423, and the sliding block 424 is threadedly sleeved over the adjustment screw rod 423.

The adjustment knob 422 is rotated, and the adjustment knob 422 drives the adjustment screw rod 423 to rotate, which can drive the sliding block 424 to reciprocate along the extending direction of the limiting groove 4210.

It should be noted that the first locking suture fixing structure 410 mentioned above may be of various specific structural forms. An example is provided below, but the present disclosure is not limited thereto. The first locking suture fixing structure 410 comprises a transverse fixing rod and a longitudinal fixing rod. The bottom of the longitudinal fixing rod is connected to the transverse fixing rod, and the locking suture can be wound around the longitudinal fixing rod after extending out from the proximal end of the first suture passing handle 311. In this way, the first locking suture fixing structure 410 can play a role of locking the locking suture. The aforementioned locking part 4240 may be a longitudinal rod fixed on the sliding block 424, and the locking suture extending out from the proximal end of the second suture passing handle 312 may be wound around the locking part 4240. In this way, the second locking suture fixing structure 420 can play a role of locking the locking suture.

It can be understood that, in this embodiment, the first locking suture fixing structure 410 and the second locking suture fixing structure 420 can simultaneously combine and then lock the two locking sutures, so as to connect the two locking sutures. Specifically, one of the locking sutures is locked to the first locking suture fixing structure 410 after passing through one second suture routing hole 112, one first suture routing hole 111 and the first suture passing handle 311. The other locking suture, after passing through the other second suture routing hole 112, the other first suture routing hole 111 and the second suture passing handle 312, is locked to the locking part 4240 of the second locking suture fixing structure 420. At this time, if the adjustment knob 422 of the second locking suture fixing structure 420 is rotated, the adjustment screw rod 423 of the second locking suture fixing structure 420 can be driven to rotate, which drives the sliding block 424 to move forward and backward along the extending direction of the limiting groove 4210, thereby tightening or releasing the locking suture locked on the locking part 4240 of the second locking suture fixing structure 420 to adjust the distance between the components connected with the two locking sutures.

In an optional implementation, the second locking suture fixing structure 420 comprises a connection seat 421, an adjustment knob 422, an adjustment screw rod 423 and a sliding block 424. The connection seat 421 is fixed to the adjustment frame 340. A limiting groove 4210 is provided on the connection seat 421, the sliding block 424 is arranged in the limiting groove 4210, and a locking part 4240 is provided on the sliding block 424. The locking part 4240 extends out through the limiting groove 4210, and the locking part 4240 is configured to be able to lock the locking suture extending out from the second suture passing handle 312, the adjustment knob 422 is connected to one end of the adjustment screw rod 423, and the adjustment screw rod 423 passes through the adjustment frame 340 and extends into the inside of the limiting groove 4210. The sliding block 424 is threadedly connected to the adjustment screw rod 423, and the adjustment knob 422 is configured to be able to drive the adjustment screw rod 423 to rotate to drive the sliding block 424 to reciprocate along the extending direction of the limiting groove 4210.

This embodiment can be applied to a surgical scene where a locking suture connected to two fastening nails or fastening components needs to be locked, and the distance between the two fastening nails or fastening components can also be adjusted, so as to assist the doctor to quickly complete the operation of closing the two tissues which are separated due to the lesion.

In addition, referring to FIG. 7, in this embodiment, the suture-locking-device implanting apparatus further comprises a suture passing tube 500, and the proximal end of the suture passing tube 500 is connected to the distal end of the suture passing handle 310. Under the suture locking condition, the locking suture is configured to pass through the suture passing tube 500 and the suture passing handle 310, so that the locking suture is protected by the suture passing tube 500; and/or, the suture-locking-device implanting apparatus further comprises a handle housing 600 and a branch tube 700, the handle housing 600 is mounted on the mounting seat 200, and the implanting handle 320 and the suture passing handle 310 are both arranged inside the handle housing 600, the branch tube 700 is inserted into the inner cavity of the distal end of the handle housing 600, and the branch tube 700 has a first branch cavity 710 for allowing the locking suture to pass therethrough and the second branch cavity 720 for allowing the implanting cable 330 to pass therethrough.

Specifically, a perforation is provided at the distal end of the handle housing 600, and the branch tube 700 passes through the perforation. The branch tube 700 has a first branch cavity 710 for allowing the locking suture to pass therethrough and the second branch cavity 720 for allowing the implanting cable 330 to pass therethrough. Both the first branch cavity 710 and the second branch cavity 720 run through the branch tube 700 along the length direction of the branch tube 700. In the condition of locking the suture, the locking suture passes through the first branch cavity 710, and the implanting cable 330 passes through the second branch cavity 720, so that the branch tube 700 can make the locking suture and the implanting cable 330 separated from each other.

In addition, if there are two locking sutures, as shown in FIG. 7, two first suture cavities 710 separated from each other can be provided, and the two locking sutures are provided as respectively passing through different first suture cavities 710, reducing the mutual interference between the two locking sutures, and at the same time, the mutual interference between the two locking sutures and the implanting cable 330 can also be reduced.

It should be noted that: in this embodiment, "and/or" means that only one of the structure of the suture passing tube 500 and the structure of the branch tube 700 may be provided, or two of them are provided at the same time.

As shown in FIG. 12, in this embodiment, a sealing seat 1000 is also provided inside the handle housing 600, the proximal end of the branch tube 700 is connected to the sealing seat 1000, and the sealing seat 1000 can avoid the blood leakage.

In addition, as shown in FIG. 8, in conjunction with FIGS. 11 to 14, in the case where an anti-reversal structure 3200 is provided between the distal end of the rotating shell 322 and the main body tube 321 of the suture-locking-device implanting device, an avoidance hole 610 configured to avoid the anti-reversal structure 3200 is formed on the housing wall surface of the handle housing 600.

Figure 5:
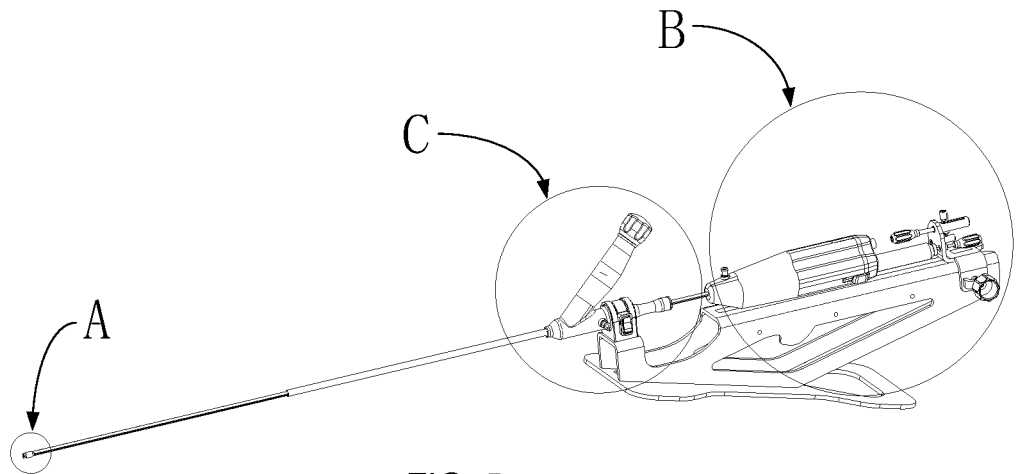
FIG. 5 is a schematic diagram of the overall structure of the suture-locking-device implanting apparatus provided by the embodiment of the present disclosure when the suture locking device is installed.
Figure 9:
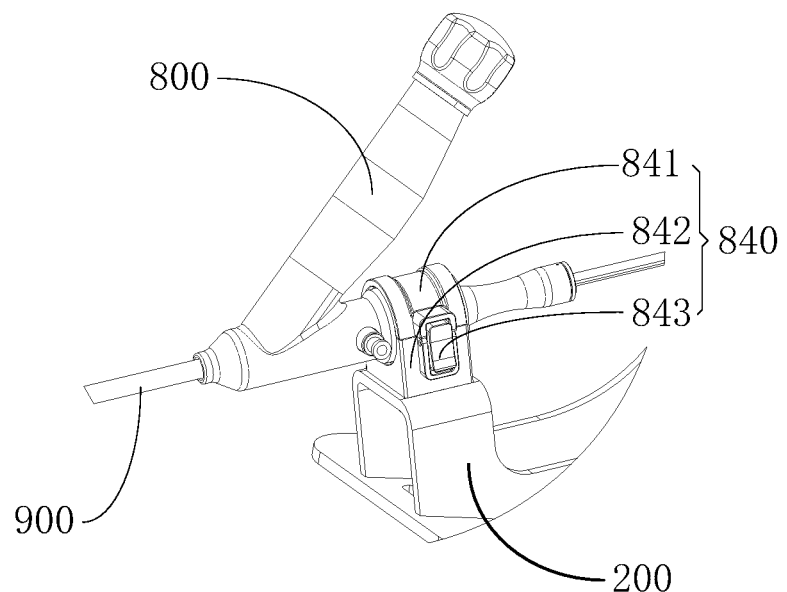
FIG. 9 is an enlarged view of the partial structure of Part C in FIG. 5.
Figure 10:
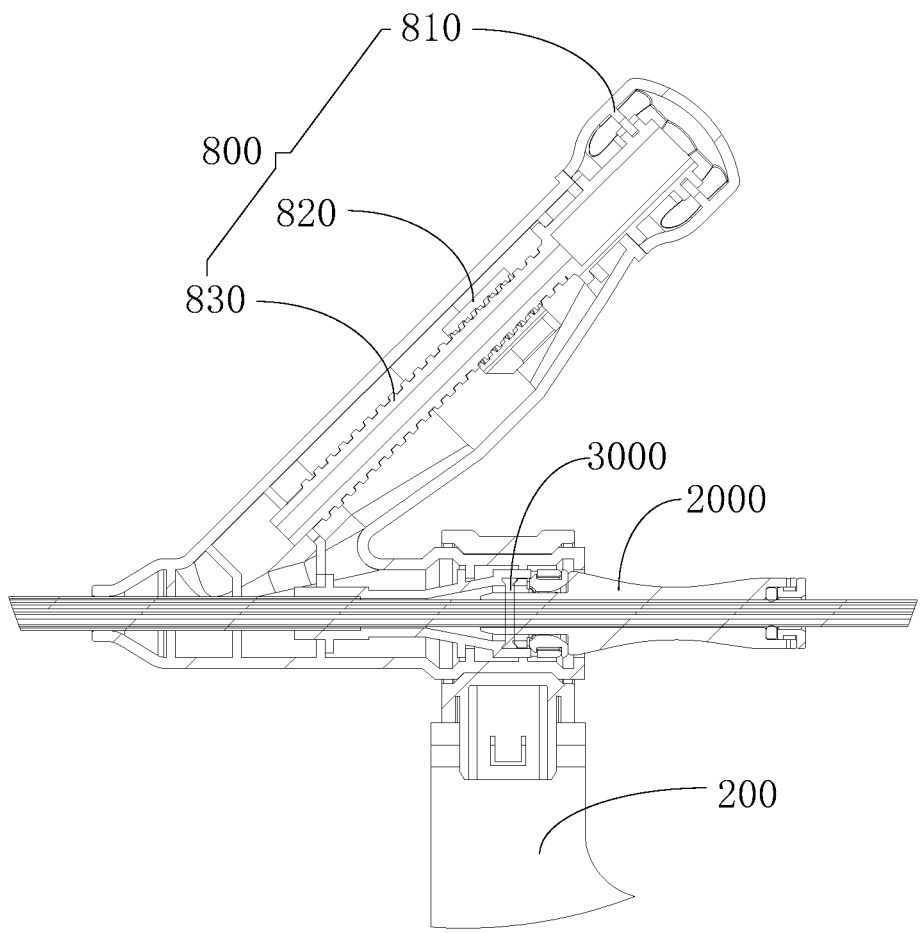
FIG. 10 is a sectional view of the bending-adjusting sheath tube mechanism shown in FIG. 9, being installed on the mounting seat.

In addition, referring to FIG. 5, FIG. 9 and FIG. 10, in this embodiment, the suture-locking-device implanting apparatus further comprises a bending-adjusting sheath tube mechanism, and the bending-adjusting sheath tube mechanism comprises a bending-adjusting handle 800 and a bending-adjusting sheath tube 900, the bending-adjusting sheath tube 900 is mounted on the distal end of the bending-adjusting handle 800, the implanting cable 330 and the locking suture are configured to pass through the bending-adjusting handle 800 and the bending-adjusting sheath tube 900, and the bending-adjusting handle 800 is configured to adjust the bending-adjusting degree of the bending-adjusting sheath tube 900.

It should be noted that, in this embodiment, the bending-adjusting handle 800 is installed on the mounting seat 200 and located in front of the implanting assembly, and the bending-adjusting handle 800 is provided with a suture passing cavity running through the bending-adjusting handle 800 in the front-rear direction. In the state of locking a suture, both the implanting cable 330 and the locking suture pass through the bending-adjusting sheath tube 900 and the suture passing cavity.

It should be noted that the bending-adjusting handle 800 can adjust the bending degree of the bending-adjusting sheath tube 900. The bending degree of the bending-adjusting sheath tube 900 is different, and the implantation position and implantation angle of the implanting cable 330 are different. That is, the bending-adjusting handle 800 can change the implantation position and the implantation angle of the implanting cable 330 by changing the bending degree of the bending-adjusting sheath tube 900.

Specifically, in this embodiment, the bending-adjusting handle 800 comprises a bending-adjusting knob 810, a bending-adjusting screw rod 820 and a bending-adjusting sliding block 830, the bending-adjusting sliding block 830 is threadedly sleeved on the bending-adjusting screw rod 820, and a bending-adjusting wire is connected between the proximal end of the bending-adjusting sheath tube 900 and the bending-adjusting sliding block 830, and the proximal end of the bending-adjusting screw rod 820 is connected with the bending-adjusting knob 810.

In this way, in actual operation, the bending-adjusting knob 810 is rotated, the bending-adjusting screw rod 820 can be rotated synchronously, and the bending-adjusting sliding block 830 slides along the length direction of the bending-adjusting screw rod 820. During the sliding process of the bending-adjusting sliding block 830, the bending-adjusting wire is tightened or released, and the bending-adjusting wire acts on the bending-adjusting sheath tube 900 to change the bending degree of the bending-adjusting sheath tube 900.

In an optional embodiment, mainly referring to FIG. 10, the bending-adjusting handle 800 comprises a bending-adjusting knob 810, a bending-adjusting screw rod 820 and a bending-adjusting sliding block 830, wherein the bending-adjusting sliding block 830 is threadedly sleeved on the bending-adjusting screw rod 820, a bending-adjusting wire is connected between the distal end of the bending-adjusting sheath tube 900 and the bending-adjusting sliding block 830, and the proximal end of the bending-adjusting screw rod 820 is connected with the bending-adjusting knob 810. The bending-adjusting knob 810 is rotated, so as to make the bending-adjusting screw rod 820 to rotate, so that the bending-adjusting sliding block 830 slides along the length direction of the bending-adjusting screw rod 820, and then the bending-adjusting wire is tightened or released, so as to adjust the bending degree of the bending-adjusting sheath tube 900, and then the implantation angle of the suture locking device 100 is adjusted. In addition, in order to facilitate the operation, as shown in FIG. 9, in this embodiment, the bending-adjusting handle 800 of the bending-adjusting sheath tube mechanism is rotatably mounted on the mounting seat 200 through the rotating structure 840. Specifically, the rotating structure comprises an upper half shell 841, a lower half shell 842 and a fastener 843. The lower half shell 842 is fixed on the mounting seat 200, and the upper half shell 841 and the lower half shell 842 are connected with each other by the fastener 843.

In actual use, by opening the fastener 843, the bending-adjusting handle 800 can be sandwiched between the upper half shell 841 and the lower half shell 842. Alternatively, by opening the fastener 843, the bending-adjusting handle 800 can also be taken out from between the upper half shell 841 and the lower half shell 842.

It should be noted that, in this embodiment, the bending-adjusting handle 800 is rotatably disposed between the upper half shell 841 and the lower half shell 842, so that the implantation angle can be adjusted more conveniently.

In an optional embodiment, the rotating structure 840 may include an upper half shell 841, a lower half shell 842 and a fastener 843. The lower half shell 842 is fixed to the mounting seat 200, and the upper half shell 841 and the lower half shell 842 are connected with each other by the fastener 843. By opening the fastener 843, the bending-adjusting handle 800 of the bending-adjusting sheath tube mechanism can be clamped between the upper half shell 841 and the lower half shell 842 or the bending-adjusting handle 800 can be taken off from between the upper half shell 841 and the lower half shell 842. The bending-adjusting handle 800 of the bending-adjusting sheath tube mechanism can be rotated between the upper half shell 841 and the lower half shell 842, so that the implantation angle can be adjusted more conveniently. In addition, referring to FIG. 10, the bending-adjusting sheath tube mechanism also comprises a supporting structural member 2000 and a sealing gasket 3000, the sealing gasket 3000 is arranged in the suture passing cavity of the bending-adjusting handle 800, and the sealing gasket 3000 is provided with a perforation. The supporting structural member 2000 is provided therein with a through cavity, and the distal end of the supporting structural member 2000 is inserted into the perforation on the sealing gasket 3000 to support the perforation. Both the implanting cable 330 and the locking suture pass through the cavity of the supporting structural member 2000, so that the implanting cable 330 and the locking suture can be easily mounted by passing, and at the same time, the internal sealing of the bending-adjusting handle 800 can be ensured to avoid the blood leakage.

The locking suture used in this embodiment is of a splicing structure in which the distal end is a polymer soft suture and the proximal end is a rigid suture. The portion formed of the rigid suture can be made of metal, but is not limited thereto, so as to facilitate the passing-mounting and the locking.

The effects that can be achieved by other structures in this embodiment that are the same as those in the first embodiment can be obtained by referring to the optional or preferred implementations in the first embodiment.

In some embodiments:

Referring to FIGS. 1 to 3, in FIGS. 1 to 3, the suture locking device 100 comprises a suture pressing housing 110, a squeezing part 120 and a driving component 130. A suture pressing cavity 1101 is arranged inside the suture pressing housing 110, the squeezing part 120 is arranged inside the suture pressing cavity 1101, and a first suture routing hole 111 and a second suture routing hole 112 are formed on the housing wall of the suture pressing housing 110. The driving component 130 is mounted on the suture pressing housing 110, the squeezing part 120 is provided with a third suture routing hole 121, wherein the first suture routing hole 111, the third suture routing hole 121 and the second suture routing hole 112 are communicated in sequence, and the driving component 130 is configured to be able to move relatively to the suture pressing housing 110, toward the cavity wall of the suture pressing cavity 1101 under the condition of locking the suture, to squeeze the squeezing part 120, so as to make the locking suture which passes through the second suture routing hole 112, the third suture routing hole 121 and the first suture routing hole 111 in sequence, squeezed between the squeezing part 120 and the cavity wall of the suture pressing cavity 1101. A snapping protrusion 122 is provided on the side wall of the suture pressing cavity 1101, and a snapping groove 123 is concavely provided on the side of the squeezing part 120 close to the snapping protrusion 122. The snapping protrusion 122 can be embedded in the snapping groove 123.

Referring to FIG. 4, in FIG. 4, the suture locking device 100 further comprises a suture cutting structure, and the suture cutting structure comprises a suture cutting shell 141 and a suture cutting blade 142. One end of the suture cutting shell 141 is sleeved over the suture pressing housing 110, and the suture cutting shell 141 covers the first routing hole 111. The suture cutting shell 141 is provided with a suture routing hole 143, and the suture routing hole 143 is communicated with the first suture routing hole 111. The suture cutting blade 142 is located inside the suture cutting shell 141. The suture cutting blade 142 is configured to cut the locking suture passing through the suture passing hole 143 and the first suture routing hole 111. The suture cutting shell 141 is also provided with an operation hole 144, and the operation hole 144 communicates with the inner cavity of the suture cutting shell 141. A first limit part 131 is provided on an end surface of one end of the driving component 130 away from the squeezing part 120. The first limit part 131 is of a polygonal convex structure.

Figure 6:
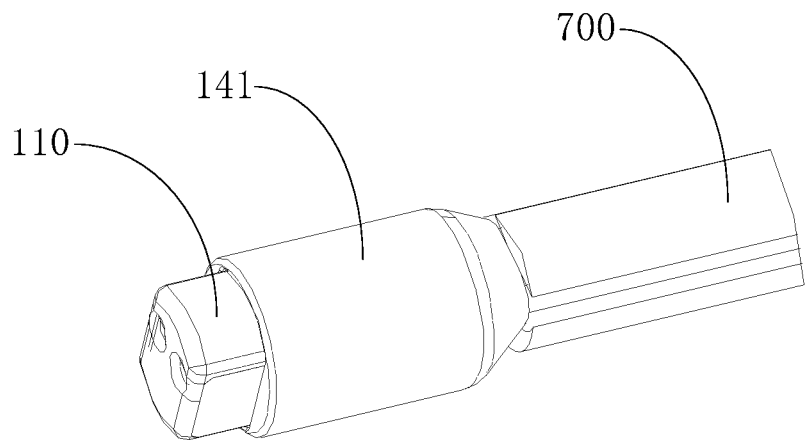
FIG. 6 is an enlarged view of a partial structure of Part A in FIG. 5.

Referring to FIG. 5-FIG. 7, in FIG. 5-FIG. 7, the implanting assembly comprises a suture passing handle 310, an implanting handle 320 and an implanting cable 330. The suture passing handle 310 and the implanting handle 320 are both mounted on the mounting seat 200. The suture passing handle 310 is provided with a suture passing cavity through which the locking suture passes. The proximal end of the implanting cable 330 is connected to the implanting handle 320, and the distal end of the implanting cable 330 is sleeved on the driving component 130. The implanting handle 320 is configured to drive the implanting cable 330 and the driving component 130 to rotate synchronously. The distal end of the implanting cable 330 is provided with a second limit part 331, the second limit part 331 is of a limiting groove structure, and the first limit part 131 and the second limit part 331 are engaged with each other, so that it is ensured that the implanting cable 330 rotates synchronously with the driving component 130.

Referring to FIG. 8, in FIG. 8, the implanting handle 320 further comprises an adjustment frame 340 and a compensation mechanism 323. The adjustment frame 340 is connected to the mounting seat 200, the compensation mechanism 323 is in transmission connection with the adjustment frame 340, and the compensation mechanism 323 is connected to the rotating shell 322. The compensation mechanism 323 comprises a compensation sleeve 3232 and a compensation knob 3231. The compensation sleeve 3232 is sleeved on the outside of the rotating shell 322. The distal end of the compensation knob 3231 is provided with a connection screw rod 3233. The adjustment frame 340 is provided with a threaded hole. The connection screw rod 3233 threadedly cooperates with the threaded hole, and the distal end of the connection screw rod 3233 is engaged with the proximal end of the compensation sleeve 3232.

Referring to FIG. 9, in FIG. 9, the bending-adjusting handle 800 of the bending-adjusting sheath tube mechanism is rotatably mounted on the mounting seat 200 through the rotating structure 840. The rotating structure comprises an upper half shell 841, a lower half shell 842 and a fastener 843. The lower half shell 842 is fixed on the mounting seat 200, and the upper half shell 841 and the lower half shell 842 are connected to each other through the fastener 843.

Referring to FIG. 10, in FIG. 10, the bending-adjusting handle 800 comprises a bending-adjusting knob 810, a bending-adjusting screw rod 820 and a bending-adjusting sliding block 830. The bending-adjusting sliding block 830 is threadedly sleeved on the bending-adjusting screw rod 820. A bending-adjusting wire is connected between the proximal end of the bending-adjusting sheath tube 900 and the bending-adjusting sliding block 830, and the proximal end of the bending-adjusting screw rod 820 is connected with the bending-adjusting knob 810.

Referring to FIGS. 11-14, in FIGS. 11-14, the implanting handle 320 comprises a main body tube 321 and a rotating shell 322, the main body tube 321 is slidably mounted on the mounting seat 200, and the distal end of the rotating shell 322 can be rotatably connected to the proximal end of the main body tube 321. The implanting cable 330 passes through the main body tube 321, and the proximal end of the implanting cable 330 is connected to the distal end of the rotating shell 322. The rotating shell 322 is configured to be able to drive the implanting cable 330 to rotate. The suture-locking-device implanting apparatus further comprises an adjustment frame 340 and a locking suture adjustment mechanism 400. The adjustment frame 340 is fixed on the mounting seat 200. The locking suture adjustment mechanism 400 comprises a first locking suture fixing structure 410 and a second locking suture fixing structure 420. The first locking suture fixing structure 410 and the second locking suture fixing structure 420 are both connected to the adjustment frame 340. The first locking suture fixing structure 410 is configured to be able to fix the locking suture extending out through the first suture passing handle 311, and the second locking suture fixing structure 420 is configured to be able to fix the locking suture extending out through the second suture passing handle 312. The second locking suture fixing structure 420 comprises a connection seat 421 and a sliding block 424. The connection seat 421 is fixedly connected to the adjustment frame 340. A limiting groove 4210 is provided on the connection seat 421, and the sliding block 424 is slidably provided in the limiting groove 4210. The sliding block 424 is provided with a locking part 4240, and the locking part 4240 extends out of the limiting groove 4210. The locking part 4240 is configured to be able to lock the locking suture extending out through the second suture passing handle 312. A middle connection rod 3211 is connected to the distal end of the rotating shell 322, and the middle connection rod 3211 extends into the inside of the proximal end of the main body tube 321. The anti-reverse structure 3200 comprises a ratchet 3201 and a pawl member; 3202, the ratchet 3201 are arranged on the outer wall of the middle connection rod 3211, the tube wall of the main body tube 321 is provided with a main body tube limiting hole 3210, and the pawl member 3202 passes through the main body tube limiting hole 3210, and the pawl member 3202 engages with the ratchet 3201.

Referring to FIGS. 15 and 16, in FIGS. 15 and 16, the inner wall of the compensation sleeve 3232 is provided with an inner pattern structure 32321 which is interlocked with the aforementioned outer pattern structure. In this way, the outer pattern structure and the inner pattern structure 32321 are snapped to each other.

Finally, it should be noted that the above embodiments are only used to illustrate the technical solutions of the present disclosure, but not to limit them. Although the present disclosure has been described in detail with reference to the foregoing embodiments, those skilled in the art should understand that it is still possible to modify the technical solutions recorded in the foregoing embodiments, or perform equivalent replacements to some or all of the technical features therein. These modifications or replacements do not make the essence of the corresponding technical solutions deviate from the scope of the technical solutions of the embodiments of the present disclosure.

INDUSTRIAL APPLICABILITY

To sum up, the present disclosure provides a suture locking device and a suture-locking-device implanting apparatus. The suture locking device and the suture-locking-device implanting device are simple and convenient in structure, which is beneficial to reduce the dependence on technology of medical staff, improve the suture locking efficiency, shorten operation time and reduce risk in operation.

What is claimed is:

1. A suture locking device, comprising a suture pressing housing, a squeezing part and a driving component,
   wherein a suture pressing cavity is provided inside the suture pressing housing;
   the squeezing part is arranged inside the suture pressing cavity, and a housing wall of the suture pressing housing is provided with at least one first suture routing hole and at least one second suture routing hole;
   the driving component is mounted at the suture pressing housing, and the driving component is configured to be able to move towards a cavity wall of the suture pressing cavity relatively to the suture pressing housing under a condition of locking a suture, so as to squeeze the squeezing part, such that a locking suture that passes through the at least one second suture routing hole and the at least one first suture routing hole in sequence is squeezed between the squeezing part and the cavity wall of the suture pressing cavity, and
   wherein the suture locking device further comprises a suture cutting structure, and the suture cutting structure comprises a suture cutting shell and a suture cutting blade, one end of the suture cutting shell is sleeved over the suture pressing housing, and the suture cutting shell covers the at least one first suture routing hole, the suture cutting blade is connected with the suture cutting shell, and the suture cutting blade is configured to cut the locking suture.

2. The suture locking device according to claim 1, wherein one end of the squeezing part is connected to an inner wall of the suture pressing cavity, the squeezing part is an elastic sheet, the driving component is configured to squeeze the squeezing part to change a distance between the other end of the squeezing part and the inner wall of the suture pressing cavity, and the squeezing part is configured to return to an initial state after the driving component is disengaged from the squeezing part.

3. The suture locking device according to claim 2, wherein the squeezing part is provided with a third suture routing hole, wherein the at least one first suture routing hole, the third suture routing hole and the at least one second suture routing hole are communicated in sequence, and the squeezing part is configured to change a distance between the other end of the squeezing part and the inner wall of the suture pressing cavity after being squeezed by the driving component, so as to squeeze the locking suture passing through the at least one first suture routing hole, the third suture routing hole and the at least one second suture routing hole.

4. The suture locking device according to claim 2, wherein a snapping protrusion is provided on a side wall of the suture pressing cavity, and the squeezing part is concavely provided with a snapping groove on one side close to the snapping protrusion, and the snapping protrusion is configured to detachably cooperate with the snapping groove.

5. The suture locking device according to claim 1, wherein an outer peripheral surface of the driving component is provided with an external thread, the suture pressing housing is provided with a threaded hole communicated with the suture pressing cavity, and the external thread is threadedly matched with the threaded hole.

6. The suture locking device according to claim 1, wherein the suture cutting shell is provided with a suture passing hole, and the suture passing hole is communicated with the at least one first suture routing hole, the suture cutting blade is located inside the suture cutting shell, the suture cutting blade is configured to cut the locking suture passing through the suture passing hole and the at least one first suture routing hole.

7. The suture locking device according to claim 1, wherein the suture cutting shell is further provided with an operation hole, and the operation hole is communicated with an inner cavity of the suture cutting shell.

8. A suture-locking-device implanting apparatus, comprising an implanting assembly and the suture locking device according to claim 1, wherein the implanting assembly is configured to implant the suture locking device into a human body.

9. The suture-locking-device implanting apparatus according to claim 8, wherein the suture-locking-device implanting apparatus further comprises a mounting seat, and the implanting assembly comprises a suture passing handle, an implanting handle and an implanting cable, the suture passing handle and the implanting handle are both mounted on the mounting seat, the suture passing handle is provided with a suture-passing cavity configured for allowing the locking suture to pass therethrough, a proximal end of the implanting cable is connected with the implanting handle, a distal end of the implanting cable is sleeved over the driving component, and the implanting handle is configured to drive the implanting cable and the driving component to rotate synchronously.

10. The suture-locking-device implanting apparatus according to claim 9, wherein the implanting handle comprises a main body tube and a rotating shell, the main body tube is slidably installed on the mounting seat, a distal end of the rotating shell is rotatably connected to a proximal end of the main body tube, the implanting cable passes through the main body tube, a proximal end of the implanting cable is connected to a distal end of the rotating shell, and the rotating shell is configured to be able to drive the implanting cable to rotate.

11. The suture-locking-device implanting apparatus according to claim 10, wherein the implanting handle further comprises an adjustment frame and a compensation mechanism, the adjustment frame is connected to the mounting seat, the compensation mechanism is in transmission connection with the adjustment frame, the compensation mechanism is connected with the rotating shell, and the compensation mechanism is configured to move back and forth relative to the mounting seat, while driving the rotating shell to rotate relatively to the mounting seat.

12. The suture-locking-device implanting apparatus according to claim 11, wherein the compensation mechanism comprises a compensation sleeve and a compensation knob, the compensation sleeve is sleeved over the rotating shell, a connection screw rod is provided at a distal end of the compensation knob, the adjustment frame is provided with a threaded hole, the connection screw rod is threadedly matched with the threaded hole, and a distal end of the connection screw rod is engaged with a proximal end of the compensation sleeve; and the compensation knob is configured to be able to drive the connection screw rod to rotate, thereby driving the rotating shell to move back and forth relatively to the mounting seat, while rotating relatively to the mounting seat.

13. The suture-locking-device implanting apparatus according to claim 9, wherein the at least one first suture routing hole and the at least one second suture routing hole, in number of two respectively, are in one-to-one correspondence, the suture passing handle comprises a first suture passing handle and a second suture passing handle, both the first suture passing handle and the second suture passing handles are mounted on the mounting seat, the first suture passing handle and the second suture passing handle are each provided therein with a suture routing cavity, the suture routing cavity in the first suture passing handle and the suture routing cavity in the second suture passing handle are respectively communicated with corresponding first suture routing holes.

14. The suture-locking-device implanting apparatus according to claim 13, wherein the suture-locking-device implanting apparatus further comprises an adjustment frame and a locking suture adjustment mechanism, the adjustment frame is fixed on the mounting seat, the locking suture adjustment mechanism comprises a first locking suture fixing structure and a second locking suture fixing structure, the first locking suture fixing structure and the second locking suture fixing structure are both connected to the adjustment frame, the first locking suture fixing structure is configured to be able to fix the locking suture extending out from the suture passing handle, and the second locking suture fixing structure is configured to be able to fix the locking suture extending out from the second suture passing handle.

15. The suture-locking-device implanting apparatus according to claim 14, wherein the second locking suture fixing structure comprises a connection seat and a sliding block, the connection seat is fixedly connected to the adjustment frame, the connection seat is provided with a limiting groove, the sliding block is slidably provided in the limiting groove, the sliding block is provided with a locking part, the locking part extends out from the limiting groove, and the locking part is configured to be able to lock the locking suture extending out from the second suture passing handle.

16. The suture-locking-device implanting apparatus according to claim 15, wherein the second locking suture fixing structure further comprises an adjustment screw rod and an adjustment knob, the adjustment screw rod passes through the adjustment frame and extends into the limiting groove, the adjustment knob is connected to one end of the adjustment screw rod, the sliding block is threadedly sleeved on the adjustment screw rod, and the adjustment knob is configured to drive the adjustment screw rod to rotate to drive the sliding block to reciprocate in an extending direction of the limiting groove.

17. The suture-locking-device implanting apparatus according to claim 9, wherein the suture-locking-device implanting apparatus further comprises a suture passing tube, the suture passing tube has a proximal end connected to a distal end of the suture passing handle, and the locking suture is configured to pass through suture passing tube and the suture passing handle.

18. The suture-locking-device implanting apparatus according to claim 9, wherein the suture-locking-device implanting apparatus further comprises a handle housing and a branch tube, the handle housing is mounted on the mounting seat, the implanting handle and the suture passing handle are both located inside the handle housing, and the branch tube is inserted into an inner cavity of a distal end of the handle housing; and the branch tube has a first branch cavity through which the locking suture passes and a second branch cavity through which the implanting cable passes.

19. The suture-locking-device implanting apparatus according to claim 9, wherein the suture-locking-device implanting apparatus further comprises a bending-adjusting sheath tube mechanism, which comprises a bending-adjusting handle and a bending-adjusting sheath tube, the bending-adjusting sheath tube is mounted on a distal end of the bending-adjusting handle, the implanting cable and the locking suture are configured to pass through the bending-adjusting handle and the bending-adjusting sheath tube, and the bending-adjusting handle is configured to adjust a bending degree of the bending-adjusting sheath tube.

* * * * *